United States Patent
Squeri

(10) Patent No.: US 8,437,830 B2
(45) Date of Patent: *May 7, 2013

(54) IMPLANTABLE ELECTROPHYSIOLOGY LEAD BODY

(75) Inventor: John Squeri, Downingtown, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/603,663

(22) Filed: Oct. 22, 2009

(65) Prior Publication Data

US 2010/0042192 A1      Feb. 18, 2010

Related U.S. Application Data

(63) Continuation of application No. 11/269,511, filed on Nov. 7, 2005, now Pat. No. 7,630,749.

(51) Int. Cl.
*A61B 5/04*       (2006.01)

(52) U.S. Cl.
USPC ............................ 600/373; 600/374; 607/116

(58) Field of Classification Search ................ 607/122, 607/116; 600/373, 374
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 4,573,480 A | 3/1986 | Hirschberg |
| 5,016,646 A | 5/1991 | Gotthardt et al. |
| 5,358,516 A * | 10/1994 | Myers et al. .................. 607/116 |
| 5,476,589 A | 12/1995 | Bacino |
| 5,519,172 A | 5/1996 | Spencer et al. |
| 5,560,279 A * | 10/1996 | Connors et al. .................. 92/5 R |
| 5,674,272 A * | 10/1997 | Bush et al. ..................... 607/122 |
| 5,676,694 A | 10/1997 | Boser et al. |
| 5,796,044 A | 8/1998 | Cobian et al. |
| 5,845,396 A | 12/1998 | Altman et al. |
| 5,879,794 A | 3/1999 | Korleski, Jr. |
| 6,159,565 A | 12/2000 | Campbell et al. |
| 6,266,563 B1 | 7/2001 | Ken Knight et al. |
| 6,366,819 B1 | 4/2002 | Stokes |
| 6,451,396 B1 | 9/2002 | Zumbrum et al. |
| 6,501,991 B1 | 12/2002 | Honeck et al. |
| 6,647,291 B1 | 11/2003 | Bonner et al. |
| 6,673,455 B2 | 1/2004 | Zumbrum et al. |
| 7,630,749 B2 * | 12/2009 | Squeri ......................... 600/373 |
| 2005/0113898 A1 | 5/2005 | Honeck et al. |
| 2005/0131511 A1* | 6/2005 | Westlund ..................... 607/126 |
| 2005/0240252 A1 | 10/2005 | Boser et al. |
| 2009/0125089 A1 | 5/2009 | Bischoff et al. |

FOREIGN PATENT DOCUMENTS

| | | |
|---|---|---|
| EP | 0 539 148 | 4/1993 |
| EP | 539148 A2 * | 4/1993 |
| WO | WO94/13358 | 6/1994 |

* cited by examiner

*Primary Examiner* — Carl H Layno
*Assistant Examiner* — Jon Eric C Morales
(74) *Attorney, Agent, or Firm* — Allan M. Wheatcraft

(57) ABSTRACT

The invention is an electrophysiology lead body comprising two or more longitudinal elements, each having an outer surface, the longitudinal elements comprising electrical insulation material, the electrical insulation material consisting essentially of fluoropolymer; at least one conductor disposed within at least one of the longitudinal elements; and a cover consisting essentially of fluoropolymer, wherein the cover surrounds the longitudinal elements.

24 Claims, 8 Drawing Sheets

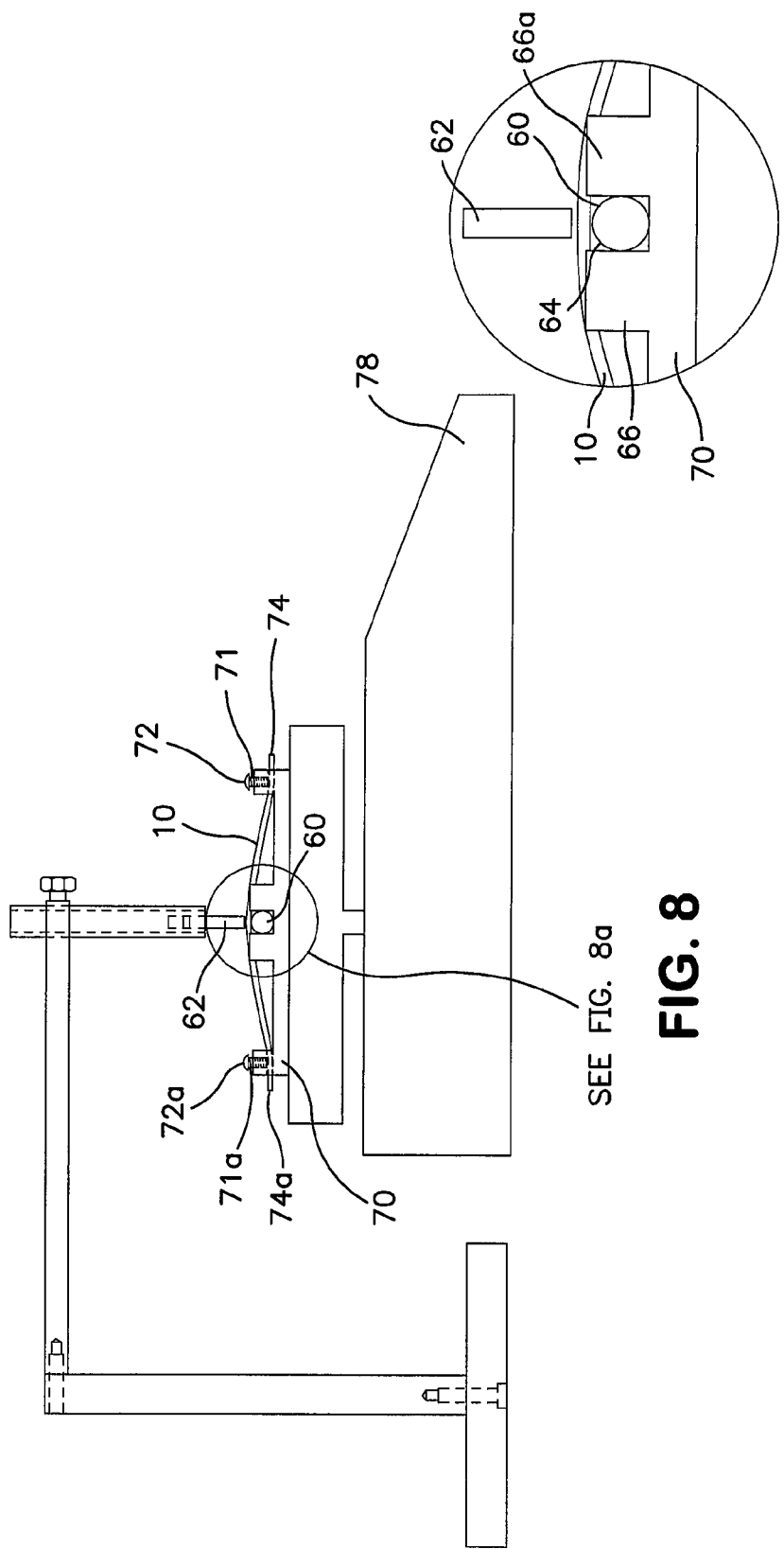

IMPLANTABLE ELECTROPHYSIOLOGY LEAD BODY

RELATED APPLICATION

The present application is a continuation application of U.S. Ser. No. 11/269,511 filed Nov. 7, 2005, is now U.S. Pat. No. 7,630,749.

BACKGROUND OF THE INVENTION

This invention relates to the field of medical electrical lead bodies for use with various implantable electronic sensing and stimulation devices such as cardiac pacemakers, implantable cardioverter defibrillators and neurostimulators, and to the method of making such implantable lead bodies.

Implantable medical electrical stimulation and/or sensing leads are well known in the fields of cardiology and neurology. Stimulation leads transmit therapeutic energy from an electrical pulse generator to the respective tissue or nerve. Sensing leads transmit electrical signals from tissue to a remote sensor. Common applications in cardiology include the treatment of various arrhythmia, (e.g. bradycardia, and tachycardia). Applications in neurology include the treatment Parkinson's Disease, epilepsy, and chronic back pain. All such medical electrical leads are herein referred to as "Implantable Leads."

Implantable leads must have excellent mechanical integrity, electrical isolation between circuits, biocompatibility, and must be flexible enough to accommodate physiologic geometry. Implantable leads must also be durable enough to accommodate the repeated flexure due to attachment and dynamic affects of anatomical features, e.g. a beating heart, a spinal cord, neck, a peripheral nerve, etc.

Known leads for use with implantable electrical stimulation devices such as cardiac pacemakers, implanted defibrillators, and neurostimulation devices are typically constructed of a lead body having an electrode assembly at the distal end, and a connector assembly at the proximal end of the lead body to connect to a pulse generator.

A lead body consists of at least one insulated electrical conductor and an outer insulation layer of tubular form coaxially surrounding the electrical conductor. Current lead body constructions for cardiac and neurological applications generally fall into two categories, coaxial and multilumen designs. A coaxial lead body typically consists of one or more helically wound coils, concentric to one another. Each coil is separated by a tubular form of insulation.

Multilumen constructions typically consist of a silicone extrusion with a desired cross section to house a combination of helically wound coils and conductors. In either coaxial or multilumen construction, a fluoropolymer material, such as Ethylene Tetrafluoroethylene (ETFE) is applied to the conductor materials. This material acts as a chemical barrier to help prevent metal ion oxidation—a reaction of the metal conductors which occurs from the release of hydrogen peroxide from macrophages.

The implantable leads described above have several disadvantages. Due to the softness of silicone, lead bodies made from that material are prone to damage during implantation and often fail (in-vivo) mechanically due to tearing, abrasion, and depression. Depression is a compressive force applied to the lead which causes the material to fracture. Silicone leads may also result in cases of acute allergic responses in some patients.

Polyurethane materials are frequently used as an alternative to silicone for added mechanical strength and lower coefficient of friction. Polyurethanes have been used in direct replacement of silicone and/or as an outer covering, or sheath for leads. Polyurethane materials and the respective leads have been known to fail due to environmental stress cracking resulting from metal ion oxidation which ultimately leads to material delamination. Such failures are known to result in pieces of insulation being released into the blood stream creating a high risk of adverse affects, including ischemic stroke.

Implantable lead wires using insulation materials other than the conventional silicones and polyurethanes have also been suggested. U.S. Pat. No. 4,573,480 describes an implantable electrode lead body in the form of a helically wound conductor having a tubular insulating layer surrounding the wire in which the tubular insulating layer is porous polytetrafluoroethylene (herein after PTFE) having a pore size limited to a maximum size described as "being essentially impervious to body fluids to prevent tissue ingrowth." This patent also teaches that the tubular porous PTFE insulating layer may alternatively be provided with an outer covering of smooth impervious material.

As the design of implantable electrical leads has progressed, there has been a general trend toward reduction in the diameter of the lead body, with further reduction desired. A lead of small body diameter may reduce the risk of internal trauma and infection, permit improved navigation through potentially tortuous geometry and simplify placement in small anatomical features. However, maintaining adequate mechanical integrity, biocompatibility, and electrical performance, which remain critical for patient safety and device effectiveness, are increasingly difficult with reductions in diameter.

SUMMARY OF THE INVENTION

In one aspect, the invention is an electrophysiology lead body comprising two or more longitudinal elements, each having an outer surface, the longitudinal elements comprising electrical insulation material, the electrical insulation material consisting essentially of fluoropolymer; at least one conductor disposed within at least one of the longitudinal elements; and a cover consisting essentially of fluoropolymer, wherein the cover surrounds the longitudinal elements.

According to another aspect, the invention includes an electrophysiology lead body comprising two or more longitudinal elements, the longitudinal elements comprising an electrical insulation material being less than about 0.003 inches thick and having a voltage strength of at least about 8000 VDC/mil; at least one conductor disposed within one of the longitudinal elements; and a cover surrounding the longitudinal elements, in which the electrophysiology lead body has a bending stiffness of less than about 10 g.

In yet another aspect, the invention provides an electrophysiology lead body comprising: two or more longitudinal elements, the longitudinal elements comprising an electrical insulation material being less than about 0.003 inches thick and having a voltage strength of at least about 8000 VDC/mil; at least one conductor disposed within one of the longitudinal elements; and a cover surrounding the longitudinal elements, in which the electrophysiology lead body has a bending radius of less than 0.5 inches.

In still another aspect, the invention comprises an electrophysiology lead body comprising two or more longitudinal elements, the longitudinal elements comprising an electrical insulation material being less than about 0.003 inches thick and having a voltage strength of at least about 8000 VDC/mil; at least one conductor disposed within one of the longitudinal elements; and a cover surrounding the longitudinal elements, in which the electrophysiology lead body has a bending stiffness of less than about 10 g In another aspect, the invention provides an electrophysiology lead body comprising two or more longitudinal elements each having an outer surface, the longitudinal elements comprising an electrically insulating material having a matrix tensile strength of at least 10,000 psi in at least one orthogonal direction; a conductor disposed within at least one of the longitudinal elements; and a cover surrounding the longitudinal elements, the cover comprising insulation material having a matrix tensile strength of at least 10,000 psi in at least one orthogonal direction.

DESCRIPTION OF THE DRAWINGS

FIG. 8 reflects the test apparatus for measuring bending stiffness.

DETAILED DESCRIPTION OF THE INVENTION

Figure 1:
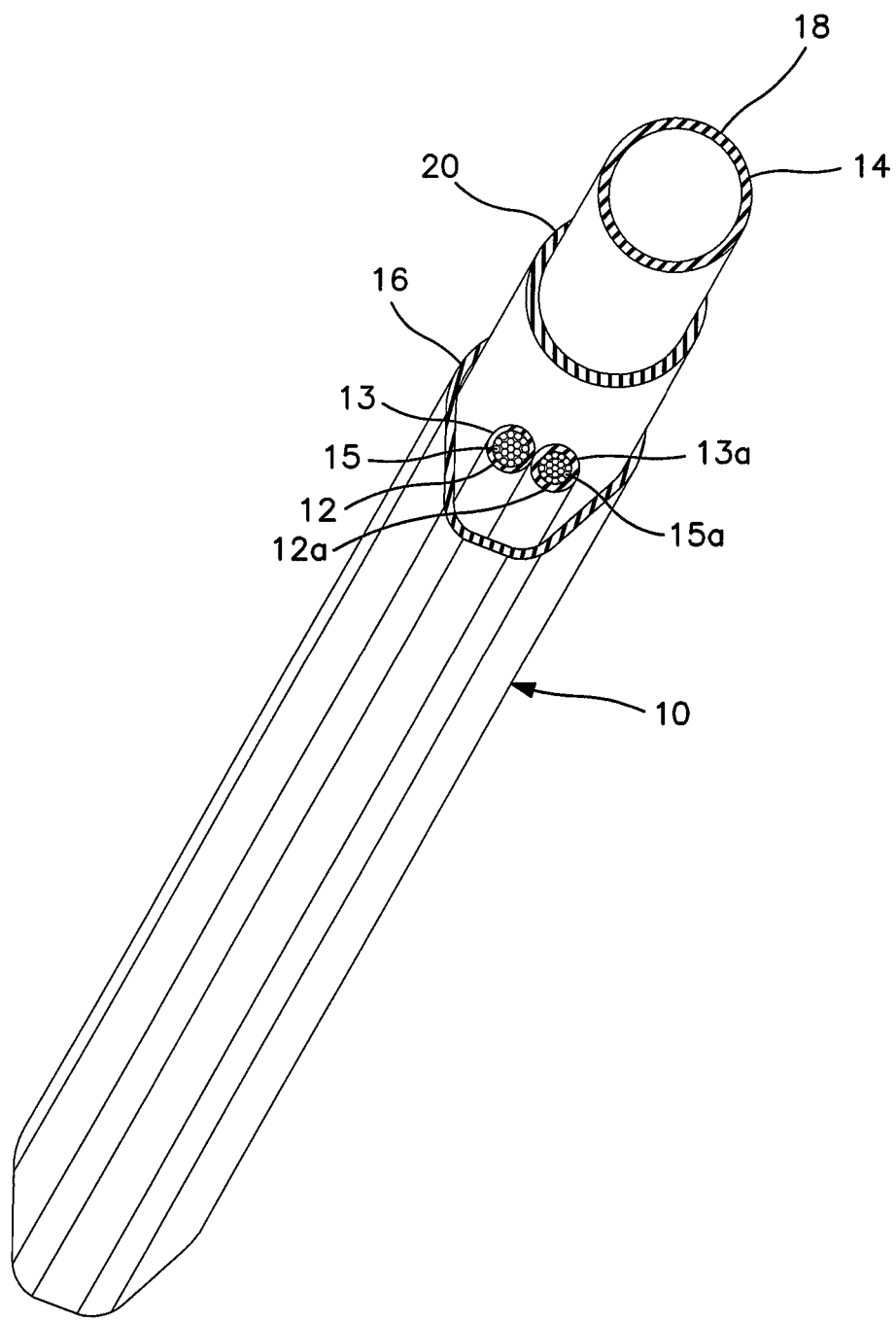
FIG. 1 shows a perspective view of implantable lead of the present invention having three longitudinal elements: a lumen and two insulated conductors.

One embodiment of the implantable electrophysiology lead body according to the present invention is depicted in FIG. 1 and includes at least two longitudinal elements. At least one longitudinal element (12, 12a) is an insulated conductor comprising a conductive material (13, 13a) and an electrically insulating fluoropolymer material (15, 15a) coaxially covering the conductive material. Optionally, the lead body may include other longitudinal or essentially parallel elements, such as one or more hollow tubes or lumen, wires, guide wires, fibers and the like (each a "longitudinal element"). Longitudinal elements comprise fluoropolymer insulation material and can have any cross-sectional shape, including but not limited to profiles that are circular, oval, triangular, square, polygon shaped or random shaped.

Figure 2:
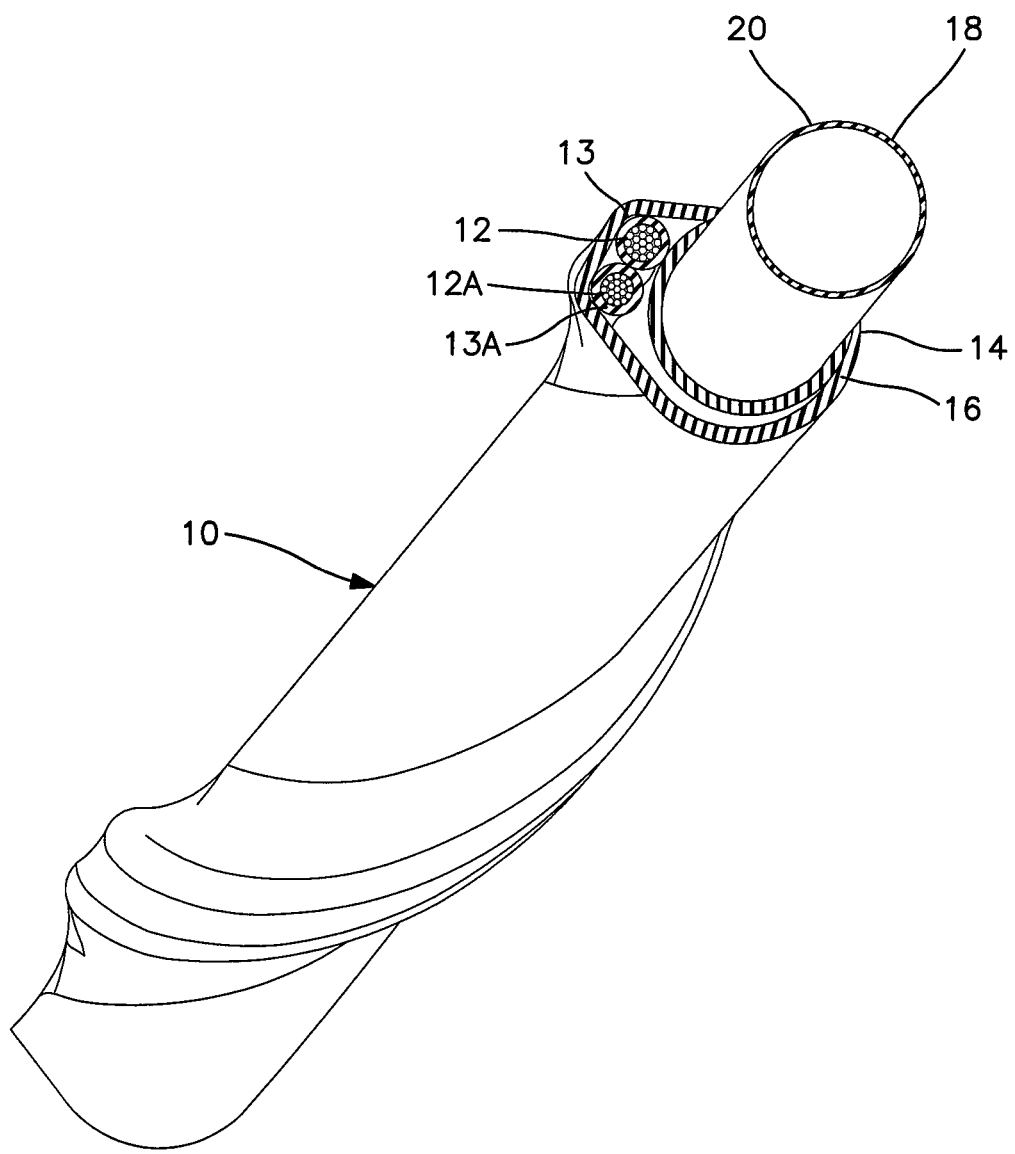
FIG. 2 shows a perspective view of a lead body in accordance with the present invention wherein the longitudinal elements include electrically insulated conductors helically wrapped around a lumen.

The term "essentially parallel" as applied to more than one longitudinal element, includes a "side-by-side" relationship (as shown in FIG. 1, as well as configurations that have longitudinally extending elements in a helical or "twisted" relationship as shown in FIG. 2 and described below.

Fluoropolymer insulation materials useful in the present invention have both high tensile strength and high dielectric or voltage strength. The high tensile and dielectric strength of the materials enables the use of very thin layers so that lead bodies according to the present invention can be surprisingly small. The highly flexible lead bodies have small bending radii and are substantially kink-resistant.

The fluoropolymer insulation materials are preferably constructed from a thin tape made from fluoropolymer film. Suitable fluoropolymer films include, for example, fluorinated ethylene propylene (FEP), ethylene tetrafluoroethylene (ETFE) and chemical modifications thereof such as EFEP (available from Daikin America, Inc., under the trade mark NEOFLON), perfluoro alkoxy resin (PFA), fluoroelastomers, etc. Porous fluoropolymers, optionally provided with a thin, non-porous coating, may be advantageously used because of their excellent flexibility. Preferably, the fluoropolymer film is ePTFE. Suitable ePTFE films can be made as taught by U.S. Pat. Nos. 3,953,566 and 4,187,390 to Gore and U.S. Pat. No. 5,476,589 to Bacino. Such fluoropolymer films are generally porous, flexible, and strong.

Most preferably, however, the fluoropolymer film is a composite comprising at least one layer of non-porous ePTFE. Non-porous ePTFE is commercially available in tape form from W.L. Gore & Associates, Newark, Del. Such non-porous ePTFE is biocompatible and combines dielectric strength of up to 8000 Vdc/mil with exceptional mechanical performance. These tapes are also characterized by high tensile strength and excellent abrasion and compression resistance. Tapes useful in the present invention have a matrix tensile strength of at least about 10,000 psi in one orthoganal direction.

The fluoropolymer film may advantageously be provided with a porous or non-porous coating of a thermoplastic such as a thermoplastic fluoropolymer, preferably fluorinated ethylene propylene (FEP). Thus, the film may also comprise a fluoropolymer laminate. Lamination can be achieved by adhering or co-joining other films, e.g., by thermally, chemically or mechanically bonding ePTFE to other materials. Specifically, the laminate includes one or more fluoropolymer sheets or films such as FEP, EFEP, PFA, PTFE, THV and other suitable fluoropolymers. Laminates comprising ePTFE and FEP films are taught in U.S. Pat. No. 6,159,565, to Campbell et al. commonly assigned herewith.

It may also be desirable to modify the fluoropolymer films used in the present invention by providing various fillers, also referred to as additives, to the film. In the case of porous polymers such as ePTFE film, fillers can be imbibed into the porosity of the film by known methods, such as the methods taught by U.S. Pat. No. 5,879,794, to Korleski. Suitable fillers include, for example, fillers in particulate and/or fiber form and can be elastomers, ceramics, metals, metalloids, carbon, and combinations thereof. Particularly useful fillers include, for example, radiopaque materials, such as certain metals (e.g. barium alloys) and carbon. The fillers can be used in combination with desired adhesive materials when imbibed into the porosity of the polymer film. It may also be desirable to metalize the film or at least a portion thereof.

A filler may be included in the matrix of the polymer itself, or contained within the voids defined by the polymeric structure, or both. Desirable fillers may also include colorants, medicants, anti-microbials, antibiotics, antibacterial agents, anti-inflammatory agents, hemostatic agents, analgesics, elastomers and mixtures thereof.

The fluoropolymer insulation material is advantageously tape-wrapped around a conductor to form an insulated conductor. The tape may be wrapped either longitudinally or helically. For example, an insulated conductor useful in the present invention may be made by longitudinally wrapping (or "Cigarette Wrapping") one or more layers of non-porous expanded PTFE film about a conductor. The film should be of length at least equal to the desired length of the conductor, and of adequate width to allow the film to be fully wrapped around the conductor surface thereby resulting in a tubular insulative covering of longitudinally oriented film. Alternatively, the film may be of adequate width to allow wrapping at least twice around the surface of the conductor if desired, thereby resulting in at least two layers of film. Preferably, the tape may be wrapped helically with successive wraps in the same or opposite directions. Combinations of helical and longitudinal wrapping may also be advantageously used.

Lead bodies of the present invention may include other longitudinal elements such as a lumen. A lumen may be made from a variety of thin, flexible fluoropolymer materials in tape form. Porous fluoropolymers, optionally provided with a thin, non-porous coating, may be advantageously used because of their excellent flexibility. A fluoropolymer lumen is preferably made by wrapping a porous expanded PTFE (ePTFE) tape that has been provided with a porous or non-porous coating of a thermoplastic fluoropolymer as described previously, around a mandrel. More preferably, the lumen is a composite, constructed by wrapping tapes of porous expanded PTFE and non-porous ePTFE.

The thin-walled tubular lumen is most preferably made from an FEP-coated non porous ePTFE film that has been cut into a tape and helically wrapped on a mandrel with the Fluoropolymer adhesive placed on the exterior of the wrapping. The non porous ePTFE layer is then covered with a porous ePTFE.

The helically-wrapped mandrell is then placed into an oven for a suitable time to thermally bond the overlapped edges of the helical wrapping together, thereby forming a tube. After removal from the oven and cooling, the resulting tube is removed from the mandrel.

The insulated conductors may include solid metal conductors, having a round or flat cross section, coils of stranded wires or drawn filled tubular conductors wrapped with fluoropolymer insulation material.

The conductive metals that are useful are well known in the art and may include any bio-compatible and bio-stable electrically conductive material that is fatigue and corrosion resistant such as gold, silver, stainless steel, platinum and platinum alloys, titanium and titanium alloys, tantalum, cobalt alloys, copper alloys, silver alloys and magnesium nickel alloys and combinations thereof. High density material, such as platinum or platinum alloys may be used to enhance fluoroscopy visibility of the lead body. MP35N, a Nickel-Cobalt base alloy that has ultra high strength, and toughness is preferred. The conductors may have surfaces of base metal or may be polished, etched or textured.

The conductors preferably include stranded wires of highly flexible, electrically conductive filaments of small diameter. In a preferred embodiment, the conductor is composed of peripheral strands, which are arranged around a central strand. The strands are tightly bundled in a cable-like fashion to form the conductor. However, it should be understood that any number of strands, or even a single strand, can be used to form the conductor of the present invention.

The outer diameter of the conductor preferably ranges from between about 0.001 inch to about 0.013 inch, and diameters of about 0.002 to about 0.006 inch are most preferred. It should, however, become apparent to those skilled in the art that the outer diameter can exceed 0.013 inch.

The conductors are covered with fluoropolymer electrical insulation material. The insulation thickness is preferably kept to a minimum, while still providing adequate voltage strength. Preferably, the fluoropolymer electrical insulation is in the form of a wrapped tape. Suitable insulated conductors comprising a standard MP35N conductor and non-porous ePTFE insulation material in thicknesses of as low as about 0.0005 inch are available in a variety of forms from W.L. Gore and Associates, Inc., Newark, Del.

The longitudinal elements are surrounded by an electrically insulative fluoropolymer cover. The cover not only provides electrical insulation, but also provides strength and kink resistance to the lead body. In a preferred aspect, an electrically insulative fluoropolymer cover comprises non-porous ePTFE. More preferably, the cover comprises at least one layer of porous ePTFE and at least one layer of non-porous ePTFE.

Although any suitable fluoropolymer film can be used (such as the films comprising the fluoropolymers mentioned above) in combination with any suitable adhesive (such as those mentioned above) if an adhesive is desired, non-porous ePTFE provided with a coating of FEP is particularly preferred. The non-porous ePTFE (or other fluoropolymer film) can be cut into a tape and wrapped about the longitudinal elements. The fluoropolymer adhesive can either face toward the elements, away from the elements, or be provided on both sides of the ePTFE film.

The fluoropolymer cover may advantageously be an ePTFE composite comprising non-porous ePTFE and porous ePTFE. The non-porous ePTFE layer contributes to high dielectric and mechanical and voltage strength to the lead body, while the porous ePTFE layer contributes to kink resistance. Preferably, the porous ePTFE layer surrounds the non-porous layer. More preferably, the cover is in the form of a first helically wrapped non-porous ePTFE tape having a matrix tensile strength of at least 10,000 psi and a second helically wrapped porous ePTFE tape layer positioned over the first layer.

For example, the first layer of the cover may comprise laminated tape of non-porous ePTFE and a thermoplastic that is preferably a non-porous thermoplastic fluoropolymer such as FEP. The laminated tape may be helically applied with overlapping edges and with the non-porous ePTFE oriented outwardly, and the thermoplastic oriented towards the conductor group. The second layer of the cover may comprise an expanded PTFE film that has been provided with a porous or non porous thermoplastic coating. The second layer is preferably wrapped around the first layer with the thermoplastic material oriented to the inside.

Multiple layers of thin tape wrapping provide greater flexibility when compared to fewer layers of thick tape. Preferably, the high strength non-porous ePTFE tape is less than about 0.001 inches thick, more preferably the tape is less than about 0.0005 inches thick, and most preferably, less than about 0.0002 inches thick. The high strength tape laminate is advantageously wrapped with an overlap to achieve a thickness of about 0.0002 inches to about 0.003 inches. A thicker cover may yield greater dielectric strength and a stronger lead body, but will increase the lead body diameter and stiffness.

In one aspect, the ICD lead body may be at least partially disposed within a sheath. As used herein, a "sheath" is a flexible tubular member intended to improve the physical characteristics of the lead body or to add functionality to it. A sheath may be used to improve the stiffness, tactile feel, friction or other physical characteristic, or promote an enhanced tissue response. For example, the sheath may be adapted for use as a drug or chemical delivery device. A sheath may be constructed of conventional materials such as silicone and polyurethane and may be constructed by molding or extruding methods known in the art. Preferably, however the sheath consists essentially of fluoropolymer and is constructed by the tape wrap process described above. The sheath may consist of a fluoropolymer composite, including porous and nonporous ePTFE. The sheath may consist of a fluoropolymer imbibed with an elastomer.

Further variations of the inventive leads will be appreciated by the skilled artisan. By providing a tape wrap about the outer surfaces of two or more longitudinal elements, it is possible to obtain a secure construction of dissimilar elements. Moreover, such longitudinal elements can be assembled without fusing, bonding or adhering the materials, which reduces lead body stiffness.

Turning to the Figures, shown in FIG. 1 is an electrophysiology lead body 10 having two longitudinally extending insulated conductors (12, 12a) and a fluoropolymer composite lumen 14 joined together, in an essentially parallel fashion, by an exterior polymer tape wrap cover 16. This tape-wrapped construction also allows two or more longitudinal elements to be joined together to form a more complex assembly. Advantageously, the longitudinal elements and cover can be combined without bonding the elements together or to the cover. The fluoropolymer film cover 16 is wrapped in an overlapping helical pattern. The film cover 16 is shown in contact with the exterior or outer surface of the insulated conductors 12, 12a and the lumen 14.

Example 1

An all-fluoropolymer lead body suitable for cardiac implantation as shown in FIG. 1 was constructed in the following manner:

A thin-walled fluoropolymer composite lumen 14 was first constructed. The lumen in this example comprised a fluoropolymer laminate having an inner layer (18) of nonporous ePTFE and an outer layer (20) of porous ePTFE. Non-porous ePTFE film of thickness equal to about 0.0005 inches, which was provided with a non-porous coating of FEP on one side, was cut into tape 0.185 inches wide. The non-porous ePTFE film has a bulk density of about 2.1 g/cc. After cutting the coated film into a tape, the tape was wrapped on a 0.040 inch diameter silver plated copper mandrel in an overlapping fashion with the FEP coated side of the tape facing away from the mandrel. The tape was wrapped at a pitch of about 20 degrees and overlapped about 25 percent. During wrapping, the tape was tensioned at 600 grams.

Porous ePTFE tape was wrapped around the non-porous ePTFE tape layer. A 0.001 inch thick porous ePTFE film having a bulk density of about 0.9 g/cc was cut into a narrow tape having a width of 0.260 inches. The tape was wrapped at a pitch of about 20 degrees at a tension of approximately 650 grams. By overlapping each successive wrap by about 50 percent, a final porous ePTFE wrap thickness of 0.002 inches was achieved. The total lumen wall thickness was about 0.003 inches. The wrapped mandrel was then heated in a convection oven set at about 390° C. for 5 minutes to melt-bond the two helically-wrapped fluoropolymer layers together.

The longitudinal elements also include two insulated conductors (12, 12a) comprising 0.006 inch diameter MP35N stranded conductors (15, 15a) with 0.001 inch thick fluoropolymer insulation (13, 13a) obtained from W. L. Gore & Associates, such as part number MCN1162. The fluoropolymer insulation had a voltage strength of at least about 8000 Vdc/mil. The insulated conductors (12, 12a) were placed adjacent to the lumen (14), with their axes roughly parallel.

The insulated conductors and fluoropolymer lumen were wrapped with non-porous fluoropolymer tape to form a cover (16). The cover was created by helically wrapping non-porous ePTFE tape laminate around the longitudinal elements. A 0.0005 inch thick ePTFE film coated on one side with FEP was first cut into a 0.225 inch wide tape. The tape was wrapped around the conductors and lumen with the Fluoropolymer adhesive to the outside of the wrap. The wrap angle was approximately 20 degrees and the tape tension was 300 g. Each wrap was overlapped approximately 25 percent by the succeeding wrap, resulting in a final thickness of the single wrap of about 0.00075 inches. After wrapping the cover, the lead body assembly was placed in a 390 degree oven for approximately 4 minutes. The mandrel was then removed from the assembled lead body.

Although in FIG. 1 the insulated conductors are shown to be substantially parallel to the lumen, other constructions and orientations are made possible by the tape wrap construction method. For example, the conductors may be helically wrapped around the lumen as shown in FIG. 2. Helical wrapping may further improve the uniformity of the bending properties of the finished lead body.

Furthermore, although the insulated conductors are shown to be similar in the figures, having substantially the similar inner and outer diameters, and as having substantially circular cross sections, it should be understood that these elements can be provided in a variety of sizes and shapes. For example, one conductor could have a much smaller outer diameter, inner diameter, or both, as compared to the second conductor. In another construction, additional longitudinal elements could be constructed within the cover, such as an additional lumen sized to accept a guidewire in a sliding relationship, or additional insulated conductors. Moreover, by appropriately choosing the orientation of the FEP side of the fluoropolymer tape, the elements may be bonded together and/or bonded to the cover.

Example 2

A second lead body, constructed using techniques similar to those of Example 1. However, this lead body is smaller and may be suitable for use in neurologic applications. As in Example 1, the lead body comprises two insulated conductors (12, 12a), but in this example, depicted in FIG. 2, the conductors are helically wrapped around a fluoropolymer lumen (14). These longitudinal elements are then covered with a fluoropolymer tape wrapping (16).

A 0.020 inch inner diameter lumen (14) was constructed by wrapping a silver plated copper mandrel with porous and non-porous fluoropolymer tape to construct a composite fluoropolymer tube. The lumen had an inner layer of non-porous ePTFE tape and an outer layer of porous ePTFE tape. The two-layer construction had a total wall thickness equal to 0.001 inches. First, a 0.0005 inch thick, 0.050 inch wide, non-porous ePTFE tape was wrapped at an angle of approximately 20 degrees around the mandrel at a tension of 175 grams with a 25 percent overlap. The tape had an Fluoropolymer adhesive oriented toward the outside of the wrap. Next, an 0.0002 inch thick porous ePTFE tape having a width of approximately 0.095 inches was wrapped at a 20 degree angle and overlapped about 25 percent with approximately 400 grams of tension to create a 0.0003 inch outer layer. The tape covered mandrel was heated in an oven set at approximately 390° for five minutes.

The insulated conductors (12, 12a) used in this example were stranded wires having a diameter of 0.003 inches. The conductors were covered by a 0.0005 inch layer of fluoropolymer insulation and obtained from W.L. Gore & Associates. The insulated conductors were helically wrapped around the lumen at a pitch of 40 degrees.

The insulated conductors and fluoropolymer lumen were wrapped with non-porous fluoropolymer tape to form a cover (16). A 0.0005 inch thick ePTFE film coated on one side with FEP was first cut into a 0.228 inch wide tape. The tape was wrapped around the longitudinal elements with the Fluoropolymer adhesive to the outside of the wrap. The wrap angle was approximately 20 degrees and the tape tension was 500 g. Each wrap was overlapped approximately 50 percent by the succeeding wrap, resulting in a final cover thickness of about 0.0015 inches. After wrapping the cover, the lead body assembly (10) was placed in a 390 degree oven for approximately 2 minutes. The mandrel was then removed from the assembled lead body.

Example 3

An elastic lead body can be constructed by using porous ePTFE tape in which at least some of the porosity is filled with an elastomer such as silicone or urethane. As used herein, an elastic lead body means a lead body that will deform at least 3% in the direction of an applied load and return to its undeformed state upon removal of such load. Methods of preparing filled or imbibed ePTFE films are taught in U.S. Pat. No. 6,673,455, and U.S. Pat. No. 6,451,396, to Zumbrum et. al and are incorporated herein by reference.

A thin-walled lumen was first constructed. The lumen comprised a fluoropolymer laminate having layers of porous ePTFE imbibed with silicone. Porous ePTFE film of thickness equal to about 0.001 inches was cut into a 0.2 inches wide tape. The tape was then wrapped on a 0.016 inch diameter silver plated copper mandrel in an overlapping fashion. The tape was wrapped at a pitch of about 25 degrees and overlapped about 75 percent. During wrapping, the tape was tensioned at 200 grams. Next, a 0.001 inch thick imbibed ePTFE film was cut into a narrow tape using a slit width of 0.25 inches. The tape was wrapped over the first pass of tape at a pitch of about 25 degrees at a tension of approximately 225 grams. An overlap of 75 percent achieved, a final wrap thickness of 0.003 inches. The total lumen wall thickness was about 0.003 inches. The mandrel was then heated in a convection oven set at approximately 150° C. for 2 minutes to cure the two helically-wrapped imbibed fluoropolymer layers together.

As in Example 2, eight 0.003 inch diameter MP35N stranded conductors with 0.0005 inch thick fluoropolymer insulation were obtained for the insulated conductor group. The conductor group was again wrapped helically around the fluoropolymer lumen.

The insulated conductors and fluoropolymer lumen were wrapped with porous, silicone-filled fluoropolymer tape to form a cover (16). The cover was created by helically wrapping porous, silicone-imbibed ePTFE tape around the insulated conductors and the lumen. A 0.001 inch thick ePTFE film was first cut into a 0.2 inch wide tape. The tape was wrapped around the conductors and lumen. The wrap angle was approximately 25 degrees and the tape tension was 200 g. An overlap of 75 percent resulted in a layer thickness of about 0.001 inches. Next, a 0.001 inch thick imbibed ePTFE film was cut into a narrow tape using a slit width of 0.25 inches. This tape was cross wrapped over the first pass of tape at a pitch of about 25 degrees and an overlap of 75 percent at 225 grams of tension to achieve a layer thickness of 0.003 inches. After wrapping the cover, the lead body assembly was placed in a 150° C. oven for approximately 5 minutes to allow curing of the layers. The mandrel was then removed from the assembled lead body.

Example 4

Figure 5:
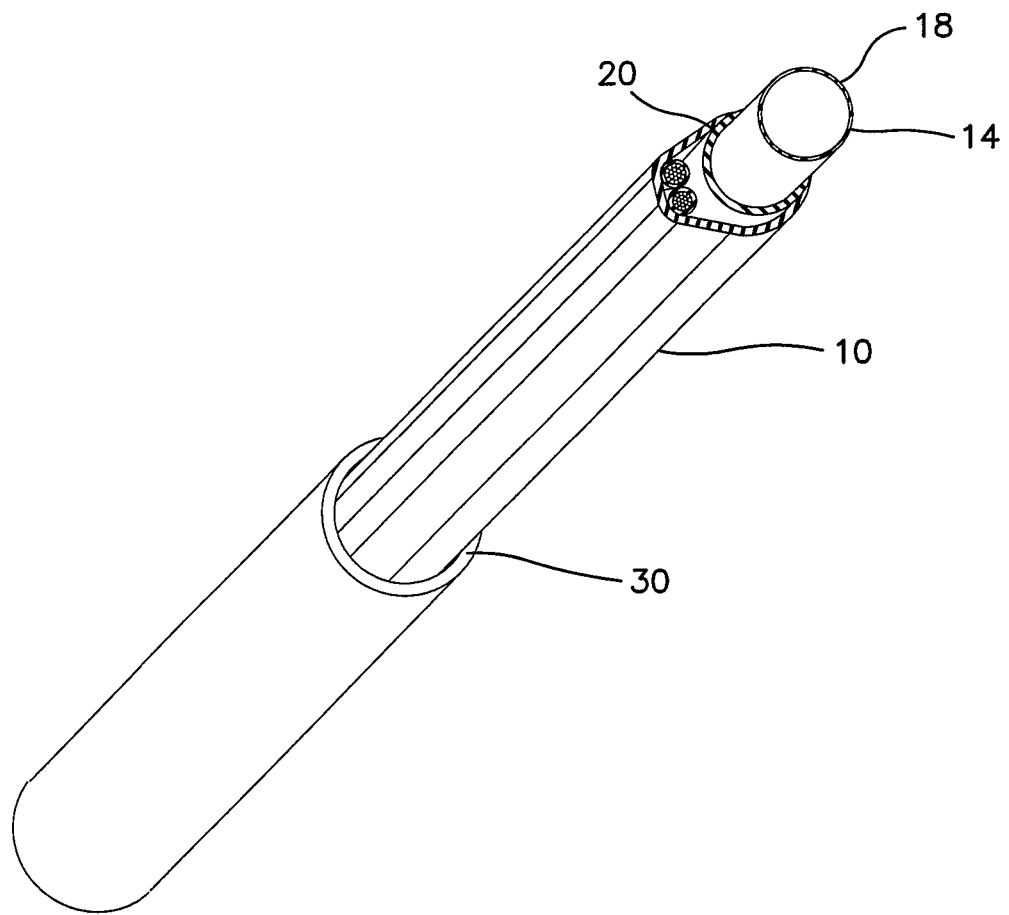
FIG. 5 shows another aspect of the invention, showing an electrophyisiology lead body disposed within a sheath.

An ICD lead body was constructed in accordance with the procedures described in Example 1. The lead body was then inserted into an all-fluoropolymer composite sheath as shown in FIG. 5. The sheath was constructed in the following manner:

A 0.001 inch thick ePTFE film was cut to 0.375 inches wide. The tape, was wrapped over a 0.055 inch diameter silver plated copper mandrel or the lead body as described in example 1 at approximately 25 degrees with a 50 percent overlap. The tape was wrapped with the adhesive facing out under a tension of 750 grams resulting in a thickness layer of 0.002 inches. The second pass of the outer sheath consisted of a 0.001 inch thick ePTFE film cut into a slit width of 0.530 inch wide. The second pass of tape was cross wrapped over the first pass at an angle of 25 degrees with a 75 percent overlap and a tension of approximately 1100 grams. This resulted in a layer thickness of 0.003 inches. A third pass of 0.0005 inch thick non-porous ePTFE, with a coating of FEP on one side, was slit into a width of approximately 0.560" wide and wrapped at an angle of 20 degrees with a 75 percent overlap and a tension of approximately 800 grams resulting in a layer thickness of 0.0015 inches. The FEP coating was facing toward the inside. The tension on the tape was approximately 700 grams. The non-porous ePTFE film had a bulk density of about 2.1 g/cc. The final construction was placed in a convection oven set at about 390 degrees Celsius for about 3 minutes. The construction was then removed from the mandrel (if a mandrel was used) and placed over the lead body as described in example 1.

Example 5

Figure 6:
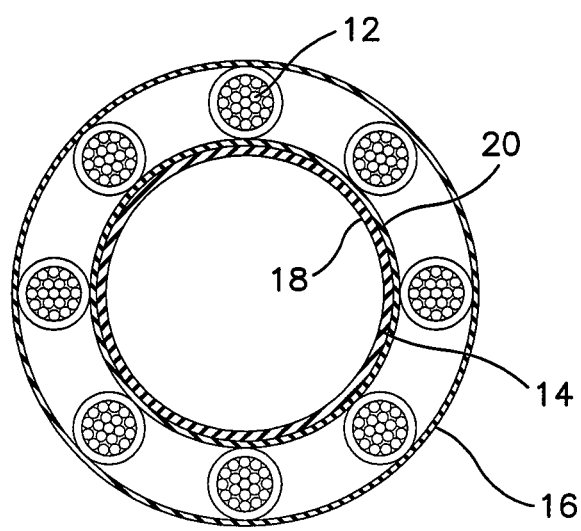
FIG. 6 shows in cross-section another aspect of the invention, in which an all fluoropolymer lead body includes 8 conductors disposed around a lumen.

In yet another example an ICD lead body was constructed having 8 conductors helically wrapped around a fluoropolymer lumen (14). The lead body cross section is depicted in FIG. 6. First, a fluoropolymer lumen was constructed in the same manner as Example 2. Eight insulated conductors were then wrapped around the lumen in a helical fasion. The insulated conductors were stranded wires having a diameter of 0.003 inches and were covered by a 0.0005 inch layer of fluoropolymer insulation and obtained from W.L. Gore & Associates. The insulated conductors were helically wrapped around the lumen at a pitch of 40 degrees. The insulated conductors and fluoropolymer lumen were wrapped with non-porous fluoropolymer tape to form a cover as described in Example 2.

The lead bodies of the present invention are produced as described above and comprised almost entirely of ePTFE, therefore, biocompatability is excellent. Furthermore, a small bending radius can be easily achieved, and the flexibility is excellent. Moreover, in the preferred lead body of the present invention, the insulation material and cover are comprised of a non-porous ePTFE structure. Therefore, film defects such as pinholes are less likely to occur, and the dielectric strength is exceptional. When the lead body of the present invention is subjected to a small bending radius, for example, bending at a radius of 10 mm, excellent flexibility and elasticity are achieved, and even with repeated bending, kinking does not occur.

Figure 3:
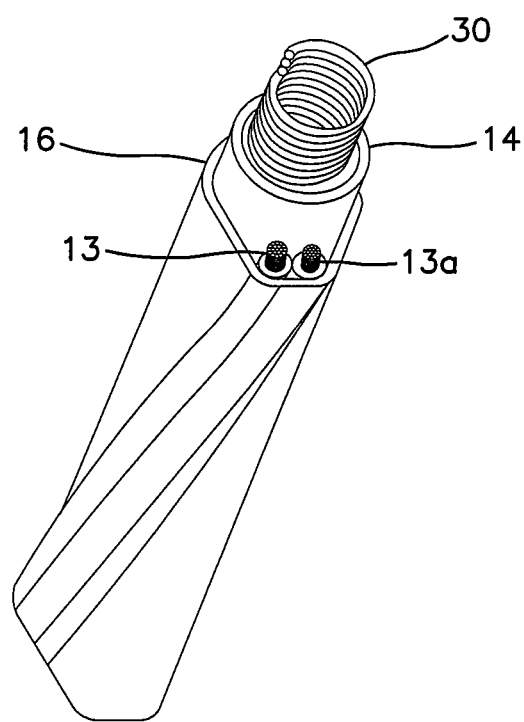
FIG. 3 shows a helically wound conductor coil disposed within the lumen of a lead body in accordance with one aspect of the invention.
Figure 4:
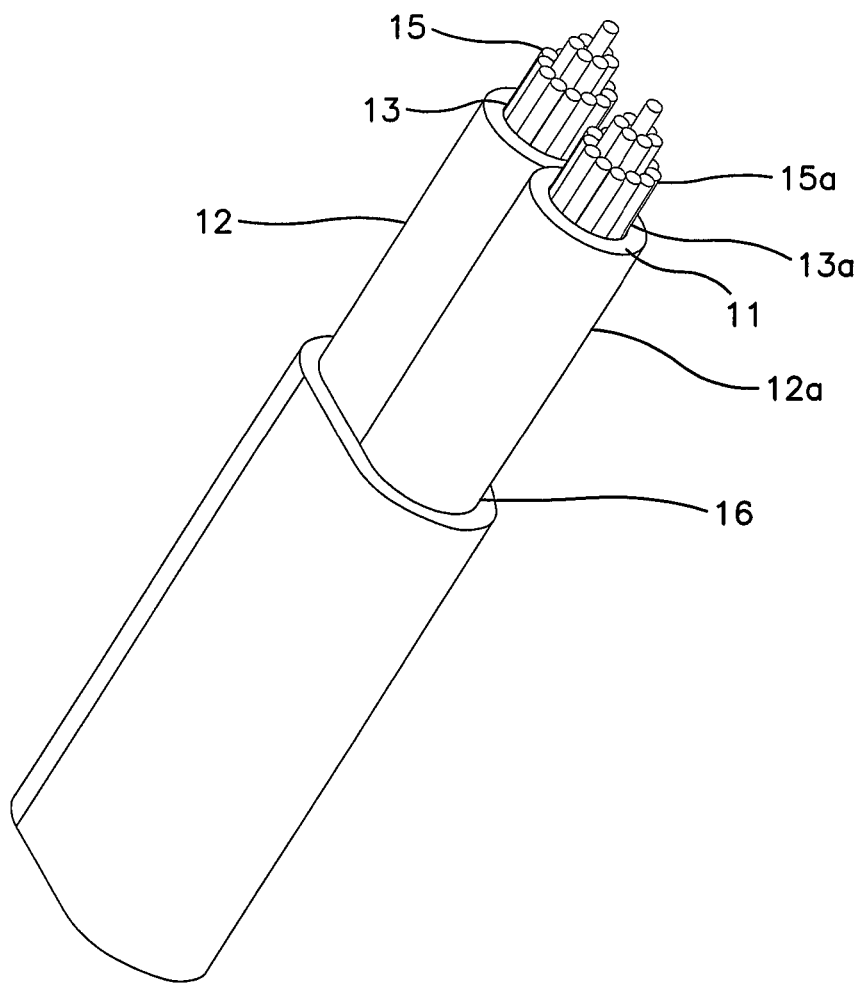
FIG. 4 shows a cross section of an alternative embodiment wherein the two longitudinal elements are insulated conductors.

The lead bodies may incorporate other elements without departing from the spirit of the invention. The composite construction techniques allow for great flexibility in the design of the lead bodies. Commonly, for example the lead will include a conductor coil (30) disposed within the fluoropolymer lumen, as depicted in FIG. 3. Other lead bodies may include only insulated conductors as longitudinal elements. For example, FIG. 4 shows an inventive lead having only two insulated conductors (12, 12a) covered by a fluoropolymer wrapping (16). The stranded conductors (13) are wrapped with fluoropolymer insulation (11) and contained within a fluoropolymer cover 16.

Test Methods

Bending Radius

Figure 7:
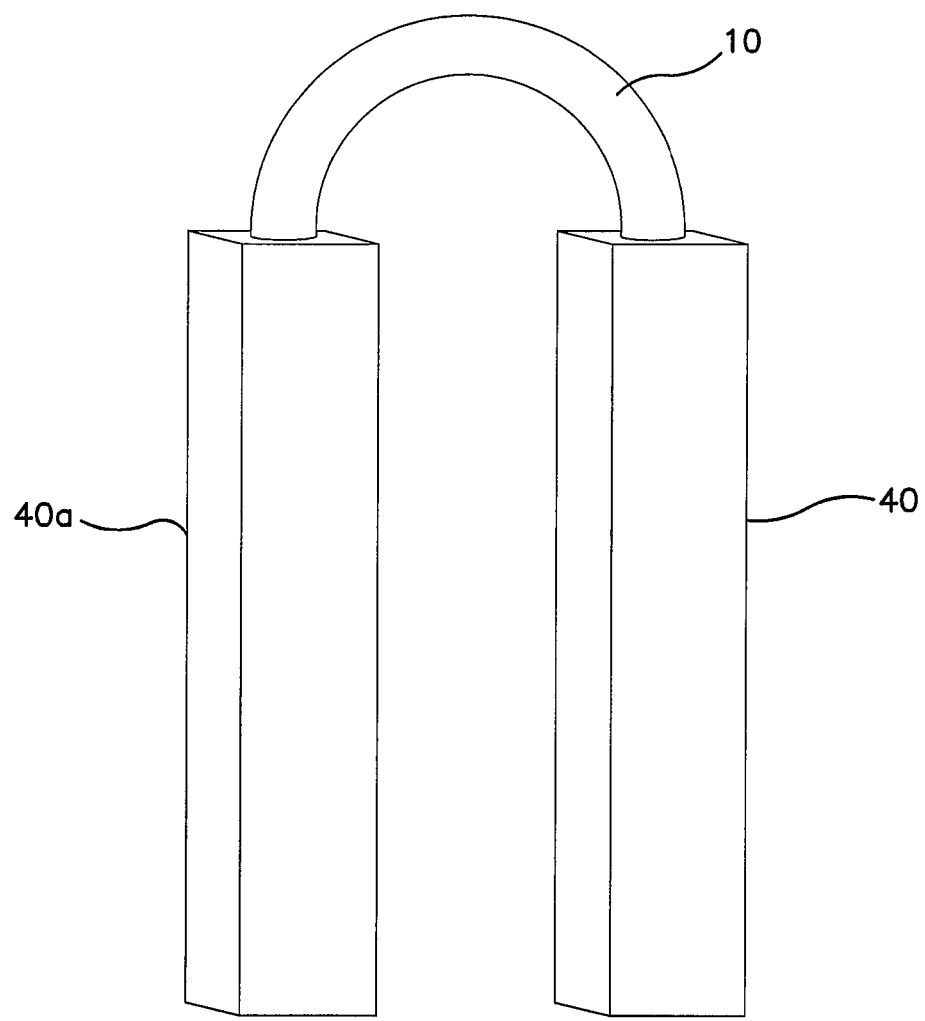
FIG. 7 shows the test apparatus for measuring bending radius.

Samples are evaluated to determine their minimum bend radius. The test was conducted as follows:

A sample was cut with a minimum length of 6 times the target bending radius. As shown in FIG. 7, the ends of the sample lead body (10) are placed in constraining devices (40, 40a), which provide a fully fixed end condition for the sample (i.e. zero rotational or translational freedom). The sample length between the constraining devices is equal to at least 5 times the target radius. The sample was bent 180 degrees such that the end s of the lead body were separated by a distance equal to the target radius. The sample is examined for visible kinking. The sample is said to have met the target bend radius if no sign of kinking appears.

Bending Stiffness

The stiffness is characterized by the force necessary to deflect a sample lead body. The bending stiffness of the inventive ICD lead body was determined through the use of a special test fixture is depicted in FIG. 8 and FIG. 8a. The fixture provides a means for bending a lead body to a predetermined initial condition. The lead body is then deflected to a final position. The force necessary to deflect the lead body from its initial position to the final position is the lead body stiffness and is measured in grams.

The test fixture comprises a base (70) having two guide blocks (66, 66a) and two end blocks (71, 71a). The guide blocks (66, 66a) contain guide channels in which the lead body moves. The end blocks (71, 71a) fix the ends of the lead body during the test. The test fixture is prepared by placing a ¼ inch diameter pin (60) between the two guide blocks (66, 66a).

The lead body (10) is passed through holes (74, 74a) in end blocks and through guide channels (64). A first end of the lead body (10) is fixed by tightening a set screw (72, 72a) installed in the first end block (71). The opposite end of the lead body is tensioned until the lead body just contacts the pin (60) and then a second mounting screw (76a) is tightened.

Next, the pin (60) is removed. In this way, a bend is formed in the center of the lead body. The fixture is then placed on a calibrated electronic scale (78) and the scale is zeroed. The lead body is then pressed downward from the top of the arch with a screw drive plunger (62). The plunger (62) has an indexing pin (not shown) or is otherwise adapted to prevent lateral movement of the lead body during movement. The lead body is depressed until it just makes contact with the base (70) of the test fixture. The bending stiffness, in grams, is read directly from the electronic scale.

Matrix Tensile Strength

Matrix tensile strength of ePTFE materials including ePTFE films is measured using an INSTRON tensile testing machine with pneumatic cord and yarn grip jaws. The machine tested 0.25 inch wide samples using a 1 inch jaw separation distance and a crosshead speed of 10 inches/minute. Matrix tensile strength of porous PTFE samples is determined by the formula:

(2.2 g/cc×tensile strength)/density of tested material, where 2.2 g/cc is taken to be the density of non-porous PTFE.

Voltage Strength (Dielectric Strength)

The following protocol was used to characterize the dielectric strength of an individual Insulated Conductor:

An insulated conductor specimen of about 15 cm is prepared and arranged such that the insulation material(s) are in direct contact with a saline preconditioning and test bath. For example, assemblies comprised of more than one insulated conductor a specimen had any outer coverings, jackets, or components, not intended to provide electrical insulation removed such that the appropriate insulation material(s) are in direct contact with the preconditioning and test baths. Specimens were preconditioned using a saline preconditioning bath of approximately 9 g/l saline at 37° C.+/−5° C. for a minimum of 10 days. Immediately prior to testing, each specimen was rinsed in distilled or deionized water, then wiped free of surface water. After preconditioning, specimens were not allowed to dry.

The specimens were immersed in a test bath consisting of approximately 9 g/l saline at 37° C.+/−5° C. The specimens were placed not less than 50 mm nor more than 200 mm from a metal reference electrode plate. The electrode reference plate had a minimum surface area of 500 mm². Care was taken to ensure that the electrodes, wire ends and terminals are electrically isolated from the test bath. All exposed metal surfaces were kept at least 20 mm from the surface of the test bath.

The electrical continuity of each conduction path was first verified by measuring the DC resistance using a resistance meter, such as a Fluke 189 digital multimeter (Fluke Corporation, Everett, Wash.). The DC voltage strength of insulation was tested for each insulated conductor. A test voltage was applied to one insulated conductor and the leakage rate was measured between that insulated conductor and the reference electrode. The leakage rate between the insulated conductor carrying the test voltage and all other insulated conductors was also measured.

An electrical safety analyzer such as the QuadTech Guardian 6000 (Quadtech, Inc., Maynard, Mass.) series testers was used to apply the test voltage, and to measure leakage current. The full test voltage was attained within 0.1 to 5 seconds of test initiation and was maintained for at least 15 seconds.

Insulated conductor insulation passed the voltage strength test only if it met the following criteria: 1) The leakage current measured between each insulated conductor and the reference electrode was less than or equal to 2 mA; 2) The leakage current measured between any two insulated conductors does not exceed 2 mA. The lumen electrical insulation test required that the leakage between the inner and out surfaces of the lumen was less than or equal to 2 mA.

| TEST RESULTS | | | | |
|---|---|---|---|---|
| | Lead Body Voltage Strength (Min. Vdc) | Minimum Bending Radius (inches) | Bending Stiffness (grams) | Lumen Voltage Strength (Min. Vdc) |
| Example 1 | 8,000 VDC | ½ | 10 | 3,500 |
| Example 2 | 4,000 VDC | 3/16 | 4 | 3,500 |
| Example 3 | 4,000 VDC | ⅛ | 5 | 10,000 |
| Example 4 | 8,000 VDC | ½ | 10 | 3,500 |
| Example 5 | 4,000 VDC | ¼ | 6 | 3,500 |

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. An electrophysiology lead body comprising:
   a) two or more longitudinal elements, each having an outer surface, said longitudinal elements comprising electrical insulation material, said insulation material consisting of wrapped fluoropolymer;
   b) at least one conductor disposed within at least one of said longitudinal elements; and
   c) a cover, said cover consisting of wrapped fluoropolymer, wherein said cover surrounds said longitudinal elements.

2. The electrophysiology lead body of claim 1, in which the conductor comprises a helical coil.

3. The electrophysiology lead body of claim 1, in which said insulation material comprises ePTFE.

4. The electrophysiology lead body of claim 3, in which aid insulation material comprises non-porous ePTFE.

5. The electrophysiology lead body of claim 3 in which said insulation material comprises ePTFE and a thermoplastic.

6. The electrophysiology lead body of claim 1, in which said cover comprises ePTFE.

7. The electrophysiology lead body of claim 6, in which said cover comprises non-porous ePTFE.

8. The electrophysiology lead body of claim 6 in which said cover comprises ePTFE and a thermoplastic.

9. The electrophysiology lead body of claim 6, in which said cover comprises a fluoropolymer laminate, said laminate including a layer of porous ePTFE and a layer of non-porous ePTFE.

10. The electrophysiology lead body of claim 1, in which said fluoropolymer is film is helically wrapped around said conductor.

11. The electrophysiology lead body of claim 1, in which said cover comprises fluoropolymer film wrapped about the outer surface of said longitudinal elements.

12. The electrophysiology lead body of claim 11, in which the film is helically wrapped about the outer surface of said longitudinal elements.

13. The electrophysiology lead body of claim 1 in which the insulation material is less than about 0.003 inches thick.

14. The article of claim 1 in which said insulation material is less than about 0.0015 inches thick.

15. The article of claim 1 in which said insulation material is less than about 0.0005 inches thick.

16. The article of claim 1 in which said insulation material is less than about 0.0002 inches thick.

17. The electrophysiology lead body of claim 1, further comprising at least one lumen disposed within said cover, said lumen consisting essentially of fluoropolymer.

18. The electrophysiology lead body of claim 17, in which said lumen comprises ePTFE.

19. The electrophysiology lead body of claim 18, in which said lumen comprises non-porous ePTFE.

20. The electrophysiology lead body of claim 1, wherein said cover is longitudinally wrapped.

21. The electrophysiology lead body of claim 1, wherein said cover is helically wrapped.

22. The electrophysiology lead body of claim 1, wherein said at least one conductor is stranded.

23. The electrophysiology lead body of claim 5, wherein said thermoplastic is FEP.

24. The electrophysiology lead body of claim 8, wherein said thermoplastic is FEP.

* * * * *

UNITED STATES PATENT AND TRADEMARK OFFICE
CERTIFICATE OF CORRECTION

PATENT NO. : 8,437,830 B2  
APPLICATION NO. : 12/603663  
DATED : May 7, 2013  
INVENTOR(S) : John Squeri Page 1 of 1

It is certified that error appears in the above-identified patent and that said Letters Patent is hereby corrected as shown below:

In the Claims:

At column 13, line 16, Claim 4: change:

"The electrophysiology lead body of claim 3, in which aid insulation material comprises non-porous ePTFE."

to

"The electrophysiology lead body of claim 3, in which said insulation material comprises non-porous ePTFE."

Signed and Sealed this  
Thirteenth Day of August, 2013

Teresa Stanek Rea  
*Acting Director of the United States Patent and Trademark Office*